(12) United States Patent
Szoka, Jr.

(10) Patent No.: US 7,465,716 B2
(45) Date of Patent: Dec. 16, 2008

(54) TARGETED DRUG DELIVERY WITH A HYALURONAN LIGAND

(75) Inventor: Francis C. Szoka, Jr., San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 382 days.

(21) Appl. No.: 10/366,275

(22) Filed: Feb. 12, 2003

(65) Prior Publication Data

US 2003/0166602 A1 Sep. 4, 2003

Related U.S. Application Data

(62) Division of application No. 09/454,811, filed on Dec. 3, 1999, now Pat. No. 6,593,308.

(51) Int. Cl.

| | |
|---|---|
| *A61K 31/728* | (2006.01) |
| *A61K 9/127* | (2006.01) |
| *A61K 48/00* | (2006.01) |
| *A61K 31/704* | (2006.01) |
| *A61K 31/7076* | (2006.01) |

(52) U.S. Cl. .................... 514/54; 424/450; 514/44; 514/114; 514/34

(58) Field of Classification Search ............... 514/54, 514/62, 1, 2, 44; 424/450; 435/458
See application file for complete search history.

(56) References Cited

U.S. PATENT DOCUMENTS 6,475,795 B1 * 11/2002 Turley et al. ............... 435/455

OTHER PUBLICATIONS

Tan et al. AUS J Biotech 4(1):38-43 (1990).*
Freemantle et al. Int J Tiss Reac XVII(4):157-166 (1995).*
Luo et al Bioconj Chem 12:1085-1088 (2001).*
McKee et al. J Clin Invest 98(10):2403-2413 (1996).*
Carbone et al. Seminars in Cancer Biology, 2004, 14: 399-405.*
Borisy et al. Proc Natl Acad Sci USA, 2003, 100: 7977-7982.*
Kunz-Schughart et al. Journal of Biomolecular Screening, 2004, 9:273-285.*
Gura Science, 1997, 278: 1041-1042.*
Voskoglou-Nomikos et al Clinical Cancer Research, 2003, 9, 4227-4239.*
Kelland et al European Journal of Cancer, 2004, 40, 827-836.*
Kerbel et al Cancer Biology & Therapy 2: 4 suppl. 1, S134-139.*
Ecke et al Goodman & Gilman's The Pharmacological basis of Therapeutics, McGraw-Hill, New York, NY. pp. 77-101.*
Vile et al Gene Therapy, 2000, 7: 2-8.*
Rubanyi et al Molecular Aspects of Medicine, 2001, 22, 113-142.*

* cited by examiner

*Primary Examiner*—Thaian N. Ton
*Assistant Examiner*—Anoop Singh
(74) *Attorney, Agent, or Firm*—Reed Smith LLP (57) ABSTRACT

The invention is a drug delivery system of a delivery vehicle having a low molecular weight hyaluronan ligand with an affinity for CD44 receptors. Preferably, the delivery vehicle is a liposome but other suitable delivery vehicles include micropspheres, micelles, emulsions, lipid discs, polymers, viral particles and viruses. The systems of the invention may further comprise a drug, which can be any anticancer agent or other therapeutic or diagnostic agent. The invention also comprises methods of delivering a drug to a cell that expresses CD44 by contacting the cell with the drug delivery system. Further methods include treating a patient with cancer and targeting drug delivery to cells that express CD44 by attaching a glycosaminoglycan ligand.

9 Claims, 3 Drawing Sheets

A. PBS

B. Free Dox 8 mg/kg

C. POPG-DOX 8mg/kg

D. HAL-DOX 8mg/kg

E. HAL-DOX 2mg/kg

F. Empty HAL+free Dox 8 mg/kg

TARGETED DRUG DELIVERY WITH A HYALURONAN LIGAND

RELATED APPLICATIONS

The present application is a Divisional of U.S. patent application Ser. No. 09/454,811, filed Dec. 3, 1999, now U.S. Pat. No. 6,593,308, issued Jul. 15, 2003, the disclosure of which is incorporated by references herein.

BACKGROUND OF THE INVENTION

1. Field of the Invention

The present invention relates to the field of targeted agent delivery and more specifically to the delivery of any therapeutic or diagnostic agent preferentially to cells expressing the CD44 receptor.

2. Description of the Related Art

Most anticancer drugs used in clinical settings are specific at a molecular rather than a cellular level. Moreover, only a small fraction of the dose reaches the target; the remaining amount of drug acts on other tissues or is rapidly eliminated. Doxorubicin is an example of one of the chemotherapeutic drugs used to treat patient with lung cancer. Doxorubicin's cytotoxicity is due to its ability to intercalate into DNA, interact with plasma membranes and take part in oxidation-reduction reactions. Thus, the cytoxic effect of this drug occurs both in normal as well as cancerous tissue and its therapeutic index is close to one. Cardiotoxicity is the major clinical adverse reaction limiting doxorubicin cumulative dosage. Toxicity and inefficient delivery remain a problem with the newer anticancer compounds being introduced into the clinic such as topotecan, gemcitabine and protein kinase C inhibitors.

Certain strategies used to deliver anticancer compounds utilize liposomes because of desirable qualities not shared by other delivery systems. Liposomes can encapsulate large quantities of drug molecules either within their aqueous interiors or dissolved into the hydrocarbon regions of their bilayers. Liposomes can also protect their contents from rapid filtration by the kidneys and degradation by metabolism, thus enhancing the drug's residence time in the body. Once taken up by a target cell, liposomes may also facilitate the cytoplasmic delivery of encapsulated drug molecules by fusing with the endosomal membrane.

So-called "conventional" liposomes have been use in cancer treatment for more than two decades to deliver a number of anticancer agents, sometimes resulting in an improved therapeutic index owing to reduced toxicity to normal tissues. However, their clinical utility has been severely limited by rapid clearance by phagocytic cells of the reticuloendothelial system (RES), by the lack of specific tumor targeting and by inappropriate release of the drug. At least two obstacles currently impede the widespread implementation of liposomes as drug carriers in vivo.

First, unmodified liposomes do not survive long in circulation, and are removed by macrophages of the reticuloendothelial system within a few hours of administration. Avoidance of this obstacle has been partially achieved by forming liposomes from saturated lipids and cholesterol, and including gangliosides or polyethyleneglycol (PEG)-derivatized lipids within the bilayer. These so-called "stealth"™ or "sterically stabilized" liposomes indeed possess reduced reactivity with serum proteins and are less susceptible to RES uptake, resulting in significant prolongation of circulation time. In addition, sterically stabilized liposomes have been shown to accumulate preferentially within tumors in animal models and in humans. It appears that the mechanism for tumor localization of liposomes involves enhanced liposome extravasation from tumor-associated vasculature, which occurs because of endothelial fenestrations and other structural abnormalities associated with tumor angiogenesis. Sterically stabilized liposomes containing doxorubicin have shown encouraging clinical activity; and doxorubicin loaded liposomes have been approved by the Food and Drug Administration (FDA) for the treatment of acquired immunodeficiency syndrome (AIDS)-associated Kaposi's sarcoma.

The second limitation is the difficulty in targeting the liposomes to tumors. Tumor-specific ligands have been difficult to identify, but even where monoclonal antibodies to specific tumor cells have been generated, rapid elimination and an immune response to the antibody have rendered the antibody-mediated targeting largely ineffectual. Further, in many instances where an antibody or other targeting ligand has been combined with the PEG coating, both long circulation and target recognition are lost. Thus, although PEG coating-appears to be necessary for prolonged liposomes survival in vivo, it simultaneously interferes with recognition of the target cell surface by the liposomes-linked antibody, forcing prior art systems to choose between targeting and survivability. Current efforts that show promise to overcome this limitation have grafted the targeting ligand unto the end of the PEG. Limitations to this approach are that a unique targeting molecule must be synthesized for each target and if the ligand is very hydrophilic it can be difficult to find a solvent that is favorable for both the ligand and the lipid.

Thus, what has been needed is a drug delivery system capable of preferentially targeting tumor cells. There is also a need for delivery vehicles that have sufficient survival in vivo to effectively deliver the payload to the desired cells. There is a further need for a drug delivery system having generic applicability to a wide range of cancers. An additional need is a drug delivery system that minimizes the cytoxicity of the drug in normal tissue while retaining its effectiveness against neoplastic tissue. This invention satisfies these and other needs.

SUMMARY OF THE INVENTION

The invention is a drug delivery system, comprising a delivery vehicle having a low molecular weight hyaluronan ligand with an affinity for CD44 receptors. The hyaluronan should have a molecular weight of less than about 100,000, preferably less than about 10,000 and more preferably less than about 5,000. In a preferred embodiment, the delivery vehicle is a liposome comprising a hyaluronan modified lipid. For example, the hyaluronan modified lipid may comprise a phosphatidylethanolamine derivative of $\beta 1,3$ N-acetyl glucosaminyl-$\beta 1,4$ glucuronide. Other suitable delivery vehicles include microspheres, micelles, emulsions, lipid discs, polymers, viral particles and viruses. The systems of the invention may further comprise a drug, which can be any anticancer agent or other therapeutic or diagnostic agent.

The attachment of the hyaluronan to the delivery vehicle depends upon the particular embodiment of the invention. For example, when the delivery vehicle is a liposome, the hyaluronan preferably comprises a lipid derivative that is incorporated into the liposome. Alternatively, the liposome may incorporate a chelating agent to immobilize a metal ion, which is then chelated by a linking agent having the gylcosaminoglycan. For example, the liposome may immobilize a nickel ion through a nitrilotriacetic acid-lipid. The hyaluronan is then covalently attached to a his-6 chelating moiety.

Alternatively, the his-6 peptide may be attached to a lipid in the lipsome and the hyaluronan may be attached to the nitrilotriacetic acid. Other means of attaching the hyaluronan to the delivery vehicle may be selected depending upon the type of delivery vehicle. Other glycosaminoglycans having an affinity for the CD44 receptor may be used in place of the hyaluronans.

The invention also comprises methods of delivering a drug to a cell that expresses CD44 by contacting the cell with a composition comprising an anticancer drug and a delivery vehicle, wherein the delivery vehicle has an attached hyaluronan having an affinity for CD44 receptors. Further methods of the invention comprise treating a patient with cancer characterized by tumor cells that express the CD44 receptor, comprising the step of administering a composition comprising an anticancer drug and a delivery vehicle, wherein the delivery vehicle has an attached hyaluronan with an affinity for CD44 receptors. Yet another method of the invention is targeting a drug to a cell expressing the CD44 receptor comprising the step of administering a composition of the drug and a delivery vehicle having an attached glycosaminoglycan with an affinity for the CD44 receptor.

The invention can also be used to target a diagnostic agent such as a radioisotope, magnetic resonance imaging agent or ultrasound contrast agent to sites in the body that express the CD44 ligand. This would permit the diagnosis of cancer and allow the extent of dissemination of the cancer through the body to be determined.

BRIEF DESCRIPTION OF THE DRAWINGS

The aforementioned advantages of the invention, as well as additional advantages thereof, will be more fully understood from a detailed description of a preferred embodiment when taken in conjunction with the accompanying drawings in which.

DETAILED DESCRIPTION OF THE INVENTION

The drug delivery systems of this invention comprise a delivery vehicle having an attached glycosaminoglycan with an affinity for CD44 receptors. Certain tumors, including many found in the lung and breast, over-express cell surface receptors that bind to glycosaminoglycans. Accordingly, delivery systems having a glycosaminoglycan targeting ligand preferentially associate with tumor cells having these receptors, leading to internalization of the delivery vehicle and its associated drug. The delivery vehicles and attached glycosaminoglcans of the invention provide a robust, versatile and efficient system for targeting drugs to a wide variety of tumors in vivo.

Hyaluronan (hyaluronic acid, HA) is a major extracellular glycosaminoglycan and is found in most, if not all, types of extracellular matrix in the mammalian body. It is a high molecular weight (>1 M Daltons) polymer composed of repeating disaccharides of $\beta 1,3$ N-acetyl glucosaminyl-$\beta 1,4$ glucuronide. The presence of an extracellular matrix enriched with hyaluronan is also characteristic of the early stages of tissue repair and remodeling in the adult and the peripheral zone of invasive tumors. Hyaluronan has been shown to influence the differentiation, migration of cells during morphogenesis, and adherence of various cell types, depending on the size and concentration of the hyaluronan and the type of cell in question. These events are mediated through receptors for hyaluronan that are present on the cell surface. CD44 is the principal cell surface receptor for hyaluronic acid. It has been suggested that the CD44 molecule, possibly a function of its activities as a hyaluronan receptor, may play a vital role in determining the fate of hematogenously disseminating melanoma cells. Indeed, many tumors are characterized by the production and accumulation of high levels of hyaluronan and neoplastic cells often exhibit substantial capacity to bind to this glycosaminoglycan.

It has recently been shown that CD44 is present on epithelial cells, some neuronal cells and hemopoietic cells, various carcinoma cell lines and melanoma, lymphoma, breast, colorectal and lung tumor cells. One of the major functions of CD44 appears to be in regulating lymphocyte adhesion to the cells of high endothelial venules during lymphocyte migration, a process that has many similarities to the metastatic dissemination of solid malignancies. These receptors are involved in the regulation of proliferation of cancer cells. It has been suggested that the CD44 molecule may play a vital role in determining the fate of hematogenously disseminating melanoma cells.

Elevated levels of CD44 have been detected in carcinomas relative to normal epithelium, a finding which was though to be consistent with the possibility that CD44 could play a part in regulating the invasive and metastatic process. Squamous metaplasia, adenocarcinoma and large cell lung cancer express CD44, which is found to be marker for these types of lung cancer. Thus lung neoplasms exhibit high expression of CD44.

The invention is a delivery vehicle with an appropriately designed ligand that will interact with a much greater avidity to cells with a high number of CD44 receptors on their surface than to cells with a low number of receptors. In preferred embodiments, the ligand comprises a low molecular weight hyaluronan. The hyaluronan oligomer has two to about 200 sugars, and preferably two to about 10 sugars. The hyaluronan should have a molecular weight of less than about 100,000, preferably less than about 10,000, more preferably less than about 5,000, and yet more preferably less than about 1,000 and more than 382. Other suitable glycosaminoglycans can be used as targeting ligands as well.

A preferred delivery vehicle in this invention is a liposome or lipidic particle. Liposomes are small vesicles composed of lipids arranged in spherical bilayers. Liposomes are usually classified as small unilamellar vesicles (SUV), large unilamellar vesicles (LUV), or multi-lamellar vesicles (MLV).

SUVs and LUVs, by definition, have only one bilayer, whereas MLVs contain many concentric bilayers. Liposomes may be used to encapsulate various materials, by trapping hydrophilic molecules in the aqueous interior or between bilayers, or by trapping hydrophobic molecules within the bilayer. In this invention, the hydrophilic targeting ligand may also provide a measure of steric stabilization to the liposome by partially impeding interactions of plasma opsonins with the vesicle surface. Gangliosides are believed to inhibit non-specific adsorption of serum proteins to liposomes, thereby prevent nonspecific recognition of liposomes by macrophages. Second, the low molecular weight oligomer of hyaluronic acid has a very weak affinity for the receptor but on a liposome it may bind only to cells with a high density of receptors where many receptors are crosslinked by multiple hyaluronans on the liposome surface. This is because of the difference between the geometry of liposome and the geometry of linear molecule. Because high affinity receptors for hyaluronic acid are greatly enriched on certain cancer cells, it was reasoned that hyaluronic acid conjugation might allow preferential targeting of liposomes to neoplastic tissues and when used as a targeting ligand on a liposome could result in altering the distribution of the targeted drug by a factor of 2-10.

In the liposome embodiments of the invention, it is convenient to synthesize hyaluronan-lipid derivatives to be incorporated into the liposome. Preferably, the mole ratio of the lipid derivatives in the lipid composition of the liposome is more than about 0.02% and less than about 50%. Exemplary lipids to which the hyaluronan may be attached include phosphatidylethanolamine derivatives such as palmitoyloleoylphosphatidylethanolamine, dipalmitoylphosphatidylethanolamine, distearoylphosphatidylethanolamine, diphytanoylphosphatidylethanolamine, N-methylphosphatidylethanolamine derivatives or phosphatidylserine derivatives. These exemplary lipids may further comprise aminopolyethylene glycols. Although these lipids are currently preferred, other lipids and liposome systems may also be used.

The systems of the invention may further comprise anti-cancer agents such as doxorubicin, topotecan, gemcitabine (2',2'-difluorodeoxycytidine), protein kinase C inhibitors, daunomycin, cisplatin, vinorelbine, cytosine arabinoside, vinblastine, vincristine, methotrexate, paclitaxel, fluoro-orotic acid, N-(phosphonyl)L-aspartic acid, tomudex, irinotecan, camptothecin, octadecylphosphocholine, ether lipids, teniposide, docetaxel, mitomycin, indoloquinones, ormaplatin, staurosporine, bryostatin, mitoxantrone, oligonucleotides, polynucleotides, and DNA. Any other suitable anti-cancer therapeutic agent may also be used. Drugs of the invention may also comprise diagnostic agents to be targeted at neoplastic tissue. Suitable drugs may also include agents useful for gene therapy. Other examples of suitable drugs for the invention include anti-inflammatory, anti-free radical compounds, pro-angiogenic, anti-angiogenic, or anti-infective agents.

The systems of the invention may be stored or administered in a variety of ways. They can be frozen, lyophilized to a dry powder or kept in solution.

The methods of the invention are especially suitable for treating patients with cancer. In preferred embodiments, the invention comprises methods for treating lung cancer. In such embodiments, the preferred route of delivery is into the airways of the lung, such as by dry powder delivery. However, other cancers having solid tumors that over-express CD44 such as breast, colorectal, prostate, sarcoma, and hepatic are also amenable to treatment with the methods of the invention.

In some embodiments, it is preferable to administer the drug systems of the invention topically or parenterally.

EXAMPLES

In Vitro

Many cells express the CD44 receptor at low levels, however CD44 expression is significantly increased in tumors. To mimic this effect, the B16F10 (murine melanoma) cells were used as tumor cells and CV-1 (monkey fibroblasts) as normal cells. To determine the influence of receptor level on the ability of cells to bind to liposomes with a gylcosaminoglycan targeting ligand, the expression of CD44 receptor was measured in these two cell lines, B16F10 and CV-1 with fluorescence cell sorting. Cells were first incubated with anti-CD44 antibodies, and thereafter with FITC-labeled anti-rat IgG. Non-specific binding of the FITC-labeled anti-rat IgG to the cells provided negative control. Both cells expressed the receptor, but the expression in B16F10 was tremendously higher (almost 100 fold) than in CV-1.

Figure 1:
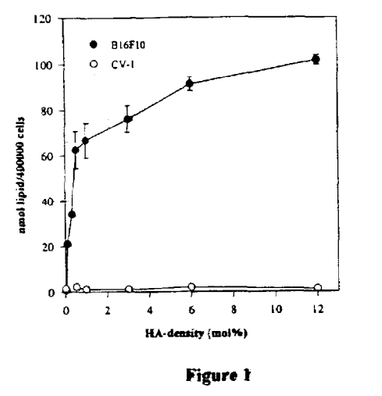
FIG. 1 is a graph showing the effect of hyaluronan tetrasaccharide-POPE ($HA_4$-POPE) density on the uptake of delivery vehicles of the invention.

Interaction of Delivery Vehicles Having a Hyaluronan Targeting Ligand with Normal and Tumor Cells In this embodiment, a liposome having a hyaluronan lipid, derivative (HAL) is used as the delivery vehicle. Small unilamelar vesicles composed of POPC/Chol (6/4 mole ratio) with different hyaluronan tetrasaccharide-POPE ($HA_4$-POPE) density were prepared and then sized by photon calorimetry scattering. The extruded liposomes exhibited a gaussian size distribution with mean diameter of 150±60 nm. As shown in FIG. 1, the presence of attached hyaluronan and the density of the hyaluronan on the liposome surface directly affects the uptake of CD44 over-expressing B16F10cells. Regardless of hyaluronan density, very little uptake was observed in the absence of hyaluronan conjugation (0 mol % HA-density, FIG. 2). The amount of total cell-associated hyaluronan liposomes increased with increasing density of liposome-conjugated hyaluronan. Even at low density (0.1-0.5 mol %) of hyaluronan, the liposomes had high affinity to the cells and showed increased uptake. The extent of uptake begins to saturate when the hyaluronan density was above 3%. No significant uptake was observed when the liposomes were incubated with control CV-1 cells, regardless the hyaluronan density.

Figure 2:
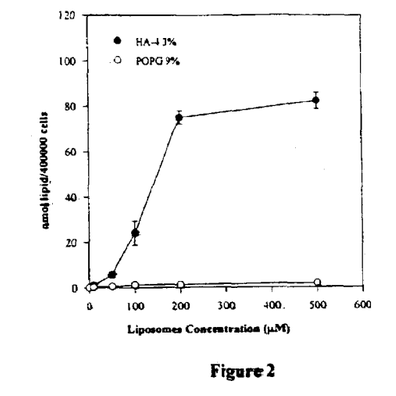
FIG. 2 is a graph showing the cell binding of liposome delivery vehicles of the invention compared to liposomes lacking the hyaluronan targeting ligand.

The amount of hyaluronan ($HA_4$-POPE) or POPG liposomes (3 or 9 mol % respectively) bound per 400,000 B16F10 cells (expressed as nanomoles of total phospholipid bound per 400,000 cells), after 3 hours of incubation at 37° C. was measured as a function of liposome concentration. FIG. 2 shows the binding of liposomes of both lipid compositions as a function of the concentration of liposomes. The binding/association of hyaluronan liposomes to the cells exhibited a classical saturation curve reminiscent of specific binding. Little binding was observed with liposomes lacking hyaluronan but containing POPG to provide a surface change as measured by the zeta potential that was the same as that of HA-POPE liposomes. This result suggests that the high affinity of the hyaluronan liposomes is because of the high affinity to the CD44 receptors on the B16F10 cells and it is not a result of electrostatic force/attraction.

Figure 3:
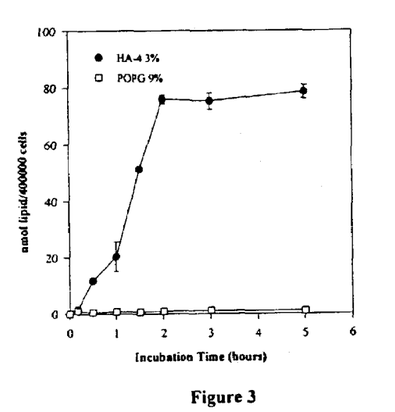
FIG. 3 is a graph showing the kinetics of uptake of liposomes having hyaluronan ligands of the invention.

FIG. 3 shows the kinetics of liposome uptake by a receptor bearing cell. B16F10 cells were incubated with 3 mol % hyaluronan liposomes for various lengths of time. Quantitative analysis of the radioactivity revealed that hyaluronan; liposomes uptake was almost linear over the first hour of incubation, was linear during the second hour and then no further increase in cell radioactivity was observed by the 3-h time point. This decline in the rate of internalization appears to derive from saturation of the uptake system rather than depletion of liposomes, since liposome concentration in the medium declined only by 30% over the course of the incubation. Therefore, hyaluronan liposomes are taken up by B16F10 cells via a saturable mechanism followed by internalization into intracellular compartments. In contrast, little uptake was observed with POPG liposomes lacking hyaluronan but with the same negative charge as hyaluronan liposomes.

Figure 4:
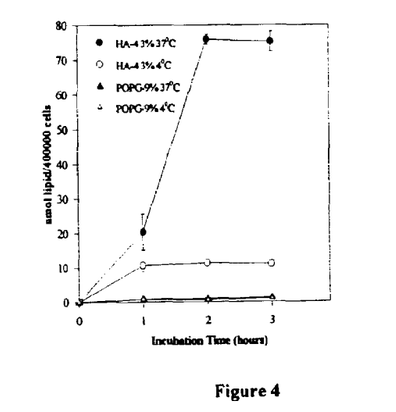
FIG. 4 is a graph comparing internalization of liposomes of the invention compared to control liposomes.

To distinguish surface bound from internalized liposomes, B16F10 cells were incubated for different periods of time with 200 μM liposomes and then washed with cold PBS to remove unattached liposomes. As shown in FIG. 4, incubation of cells at 4° C. for increasing periods of times with hyaluronan liposomes reached to a steady-state/saturation value at the first period examined after 1 hour. In contrast, at 37° C. the total uptake of liposomes was enhanced during the first two hours of incubation until a steady-state value was obtained after 2 hours. The kinetics of total association (uptake) of hyaluronan liposomes with cells was significantly faster at 37° C. than at 4° C. At 37° C., the total uptake of liposomes was enhanced suggesting that a significant fraction of the cell-associated liposomes was endocytosed. Since hyaluronan receptor binding proceeds at both 4 and 37° C., but endocytosis occurs only at the latter temperature, we interpret these data to suggest that the hyaluronan-conjugated liposomes are endocytosed only at the higher incubation temperature. Little uptake was observed with POPG liposomes in either temperature.

Figure 5A:
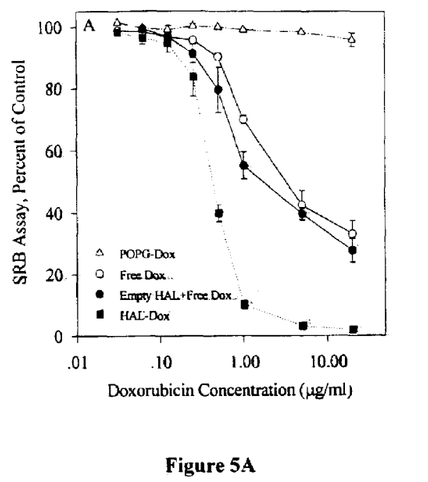
FIGS. 5A and 5B are graphs comparing the DOX dose dependence cytotoxicity of DOX encapsulated in delivery vehicles of the invention and free DOX.
Figure 5B:
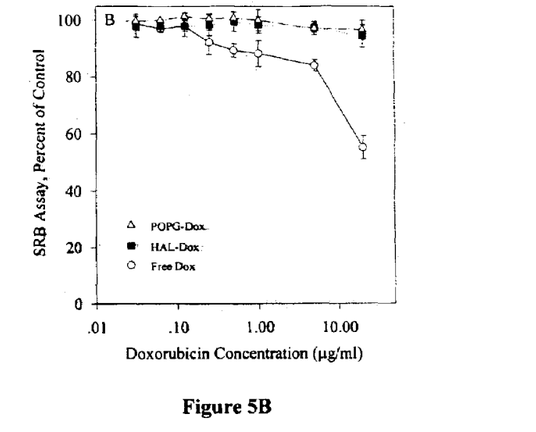

6A). The $IC_{50}$ value for DOX-loaded HAL (0.45 μg/ml, 0.78 μM) was 8-9-fold less than that for free DOX (3.7 μg/ml, 6.4 μM). In contrast, cells incubated for 3 hours with non-targeted liposomes containing DOX were not appreciably inhibited. Moreover, the HAL had no intrinsic cytotoxicity since the cytotoxicity of empty HAL plus free DOX is similar to that of free DOX alone. To examine the specificity of the HAL we treated CV-1 cells with the three formulations. CV-1 cells express a very low level of CD44. FIG. 5B shows that the sensitivity of the CV-1 cells to DOX is significantly lower then that of B16F10 cells, and unlike the case of the B16F10 cells, there was a reduction rather than an enhancement of cytotoxicity of DOX by encapsulating the drug in HAL. Furthermore, the cytotoxicity of both the HAL and POPG liposomes was. similar, confirming the low interaction of the liposomes with CV-1 cells.

Confocal microscopy of the cells after 3 hours incubated with either DOX or HAL=DOX encapsulated in HAL containing the Rh-PE shows significant drug and targeted liposomal lipid in the B16 cells.

In Vivo

Biodistribution of Hyaluronan Liposomes

The distribution of hyaluronan liposomes (HAL) labeled with an iodinated phospholipid (Barron et al., 1997) was measured in Balb/c mice 30 minutes after intravenous injection of 1 μmole total lipid in 0.1 ml PBS. The lipid composition examined consisted of HA-POPE/POPC/Chol 3/60/40 mole ratio. Sonicated vesicles were prepared with a mean diameter of 140±60 nm. Control vesicles with a composition

TABLE 1

Effect of temperature on the uptake of liposomes.

| Incubation condition | 1 hour incubation | | 2 hours incubation | | 3 hours incubation | |
|---|---|---|---|---|---|---|
| | cell-associated liposomes | % endocytosed | cell-associated liposomes | % endocytosed | cell-associated liposomes | % endocytosed |
| 4° C. | 10.7 | 0 | 11.3 | 0 | 11.1 | 0 |
| 37° C. | 20.4 | 48 | 75.9 | 85 | 75.2 | 85 |

In Table 1, radiolabeled liposomes were incubated with 400,000 cells/ml at 4° C. and 37° C. for 1, 2 and 3 hours. The amount of cell-associated liposomes at 4° C. for each time was compared to the cell associated material at 37° C. The amount of cell association is expressed as nmoles of total phospholipid taken up per 400,000 cells. The column % endocytosed represents the percent of liposomes internalized at the end of each incubation as calculated by dividing the total cell associated counts at 37° C. minus radioactivity of the amount bound at 4° C. by the total cell associated material. Uptake was inhibited by high molecular weight hyaluronan (50% at 10 nM) and pretreatment of the cells with the anti-CD4 antibody.

In-vitro Cytotoxicity of Liposome Encapsulated DOX to Normal and Tumor Cells

FIGS. 5A and 5B show the DOX dose dependence cytotoxicity determined after treatment of B16F10 and CV-1 cells with non-encapsulated DOX and DOX-loaded HAL. As shown in FIG. 5A, the cytotoxicity at 24 hours of DOX-loaded HAL after a 3 hour exposure followed by washing and replacement of the medium with drug-free medium was greater than for free DOX under the same conditions (FIG.

of POPG/POPC/Chol 9/60/40 mole ratio were prepared in a similar fashion and had a diameter of 130±50 nm. The surface charge on the control vesicles was equivalent to the surface charge on the HAL vesicles. The animals were sacrificed 30 min after injection and the organs removed, weighed and the radioactivity in each organ determined by gamma scintillation spectrometry (Table 2).

TABLE 2

Biodistribution of HAL and POPG liposomes by intravenous injection 30 min post-injection (n = 4)

| Organ | HAL vesicles | HAL STDev | POPG vesicles | POPG STDev |
|---|---|---|---|---|
| Blood | 49.7 | 10.4 | 57.8 | 4.1 |
| Heart | 2 | 1 | 2.3 | 0.4 |
| Lung | 2.4 | 0.4 | 2.5 | 0.3 |
| Liver | 19.7 | 1.3 | 20.4 | 5.3 |
| Spleen | 7.7 | 2.4 | 9 | 2.7 |
| Kidneys | 2.4 | 0.7 | 2.3 | 0.5 |

There was no significant difference in the organ distribution between the two preparations in these normal (non-tumor bearing) mice. Moreover, a substantial fraction of the injected dose remained in the blood. This is very encouraging since in order to target to lung tumors the HAL must remain in the circulation and not be eliminated by hyaluronan receptors in the liver.

Chemosensitivity Assay

The cytotoxic effect of free DOX or Liposomes-encapsulated DOX on the cells was assayed colorimetrically by the sulforhodamine B (SRB) staining. A sample containing 16,000 B16F10 or 25,000 CV-1 cells (from an exponentially growing culture) in 100 µl aliquots were plated onto 96-well flat bottom microtiter plates. The culture plates were incubated for 24 hours at 37° C. and 5% $CO_2$ and then the medium in each well was replaced with 100 µl serum-free and antibiotic-free medium containing various concentration of free or liposome-encapsulated DOX. For each 10-fold increase in drug concentration, four drug concentration levels were tested. Each test was performed in triplicate wells and was repeated in an independent experiment at least once. The cells were incubated for 3 hours (transient protocol) or 24 hours (continuous protocol) at 37° C. and 5% $CO_2$. For samples where the drug was removed at 3 hours, complete medium lacking drug was added and the incubation was continued for 24 hours at 37° C. and 5% $CO_2$ (transient protocol). At the end of the incubation period, the cells were washed once with complete (growth) medium and fresh 100 µl of complete drug-free medium was added to each well. The cultures were fixed by gently layering 25 µl of ice-cold 50% TCA (4° C.) on top of the growth medium in each well to produce a final TCA concentration of 10%. The cultures were incubated at 4° C. for 1 h and then washed and analyzed for SRB staining of the monolayers as described. The measurement of the absorbance of the SRB at 564 nm in the monolayers was determined by an Optimax microplate reader (Molecular Devices, Sunnyvale, Calif.). Each experiment was repeated twice in triplicate (n=6).

Confocal Microscopy

Confocal fluorescence microscopic methods may be used to visualize the location of fluorescent liposomes in cells that express green fluorescent proteins. The technique is employed to determine the location of the liposomes and doxorubicin in relation to the target B16 cells. In the following example of this technique, a complex was administered between cationic liposomes with a plasmid containing a green fluorescence protein reporter gene. In this example labeled with Rh-PE the GFP was expressed in only a small portion of the cells. Fluorescent lipid was visualized 24 hours after intratracheal administration, with co-current visualization of a cell transfected with a plasmid encoding a GFP. Lung structure was preserved using low melting point agarose to fill the lung air space, a protocol which fixes the lung tissue. IV administration of fluorescent lipoplex resulted in homogenous distribution of the liposomes throughout the lung. Fluorescent lectins were used to stain lung epithelium and anti CD31 to stain endothelium. The nucleus can be stained with one of several DNA stains (from Molecular Probes, ToPro-1, YoPro-3, and LDS-751). For visualization of tumors in mouse lung, the GFP B16F10 melanoma cell line available from AntiCancer, Inc. (San Diego, Calif.) may be used. High magnification (600×) of mouse lung epithelial cells transfected with a green fluorescent protein plasmid after intratracheal administration of cationic lipoplex shows that rhodamine-PE lipid persists 24 hours after administration. Rhodamine-PE was incorporated into cationic lipoplex and administered intravenously. A green fluorescent lectin stain was injected into the mouse tail vein at the time of sacrifice, for anatomic reference.

Establishment of B16F10 Lung Metastases Model.

The drug delivery systems of this invention can be tested in the B16F10 lung metastases model. The number of B16F10 tumor nodules was enumerated in the lung of syngeneic C57/BL6 mice 14days after intravenouss injection into the tail vein of $1 \times 10^5$, $3 \times 10^5$ and $1 \times 10^6$ B16F10 cells/mouse in a volume of 0.2 mL PBS. These cell numbers were used because they span the range reported to give a countable number of nodules in previous investigations. The animals were sacrificed and the lungs were removed 14 days post inoculation of B16F10 cells, and then fixed in Bouin's solution. The visible tumor nodules were assessed and counted under dissecting microscope. N=9 per group. The dose of $3 \times 10^5$ cells/mouse yielded a suitable number of nodules to provide an adequate statistical analysis. Thus, $3 \times 10^5$ cells/mouse were selected as the innoculum for subsequent studies. The distribution of hyaluronanliposomes in B16F10 tumorial mice was measured on day 14 after innoculation. The distribution of hyaluronan liposomes labeled with an iodinated phospholipid was 3 hours after intravenous injection of 1 µmole total lipid in 0.1 ml PBS. The lipid composition examined was the same as in the biodistribution studies described above. The animals (n=7) were sacrificed 3 hours after injection, the organs removed, the lungs were fixed in Bouin's solution and the radioactivity in each organ determined by gamma scintillation spectroscopy (Table 3).

TABLE 3

Biodistribution at 3 hours of post injection of HAL and POPG liposomes in C57/BL6 mice with B16F10 tumors.

| Organ | HAL vesicles | HAL STDev | POPG vesicles | POPG STDev |
|---|---|---|---|---|
| Blood | 19.9 | 3.0 | 20.2 | 9.2 |
| Heart | 0.3 | 0.1 | 0.5 | 0.2 |
| Lung | 6.2 | 0.8 | 1.2 | 0.3 |
| Liver | 11.6 | 0.9 | 14.0 | 2.0 |
| Spleen | 4.5 | 0.7 | 1.3 | 0.2 |
| Kidneys | 0.8 | 0.4 | 1.8 | 0.4 |

The accumulation of HAL In the lung, is about 5 time higher than that of the POPG liposomes. Thus HAL can accumulate in lungs that contain tumor cells that express the CD44 receptors to a greater extent than non-targeted liposomes of the same diameter, surface change, and ones all lipid composition. There was a significantly greater (p<0.001) level of HAL liposomes compared to control liposomes in the lung. There was no significant difference in any of the other organs examined.

To determine if the HAL liposomes preferentially distributed in tumor nodules, the radioactivity in the removed nodules and in the remainder of the lung which lacked visible nodules was determined. Most, 84.8±2.6%, of the radioactivity from HAL injected animals was found in the nodules. In the case of the control liposomes, only 48.8±4.1% of the counts were found in the nodules. Thus injection of HAL results in more liposomes in the tumor nodules: HAL (6.2× 0.85)=5.8%; POPG (1.2×0.48)=0.58%. Thus, the HAL accumulate in the nodules 10 fold more than do conventional liposomes. This result substantiates the ability of the HAL to target to tumor sites and highlights the utility of the composition for use as a diagnostic reagent. The radioactive 125I used in this experiment could be replaced by other radioisotopes commonly used in diagnostic imaging such as gallium 67, technetium 99 mTc or indium 111. The hyaluronan ligand when incorporated into a liposome that contains a Magnetic Resonance Imaging shift reagent on the liposome surface such as gadolinium or into a liposome that has a ultrasound contrast composition could be used for the diagnosis of cancer.

Chemotherapy of C57/B16 Mice with B16F10 Lung Tumors

The chemotherapeutic efficacy of doxorubicin delivered in various forms in the B16F10 lung tumor model was compared by counting the nodules on day 14 after innoculation of mice with B16F10. The tumored mice were treated on day six. The animals were sacrificed and tumor nodules: counted on day 14. The effect of dox-loaded HAL was compared to the therapeutic efficacy of free drug, free drug and empty HAL, POPG vesicles containing dox, and to dox-loaded HAL at drug concentration of 2 mg/kg. A statistical analysis using a multiple group comparison (two way ANOVA) and the Fisher's PLSD test and showing that HAL dox at 2 and 8 mg/kg vs. PBS had P-values of 0.0001, and a P value of 0.01 between HAL dox vs. free dox, between the POPG-Dox vs. PBS, P-value=0.0001, and P-value>0.5 between HAL-dox and POPG-dox is shown in Table 4.

TABLE 4

Effect of various treatments on number of tumor nodules appeared in lung of tumoral B16F10 mice 14 days post-inoculation of B16F10 cells. N = 9 for each group

| Treatment group | # nodules Mean | # nodules Median | Statistic (p-value) Comparison to: PBS | Free drug |
|---|---|---|---|---|
| Vehicle (PBS) | 102.00 ± 91.38 | 89 | — | 0.0305 |
| Free drug | 56.11 ± 49.48 | 45 | 0.0305 | — |
| Empty HAL + Free drug | 31.11 ± 23.20 | 19 | 0.0012 | 0.2304 |
| POPG-Dox | 13.44 ± 9.46 | 13 | <0.0001 | 0.0436 |
| HAL-Dox | 1.11 ± 2.26 | 0 | <0.0001 | 0.0103 |
| HAL-Dox 2 mg/kg | 2.89 ± 2.47 | 2 | <0.0001 | 0.0128 |

Figure 6:
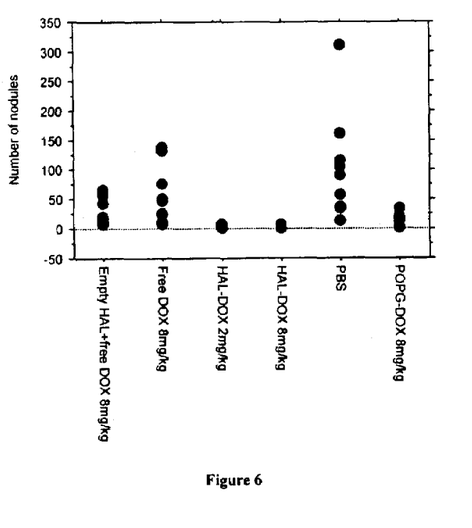
FIG. 6 is a scatter graph of the number of tumor nodules following treatment with a delivery vehicle of the invention compared to free drug.
Figure 7:
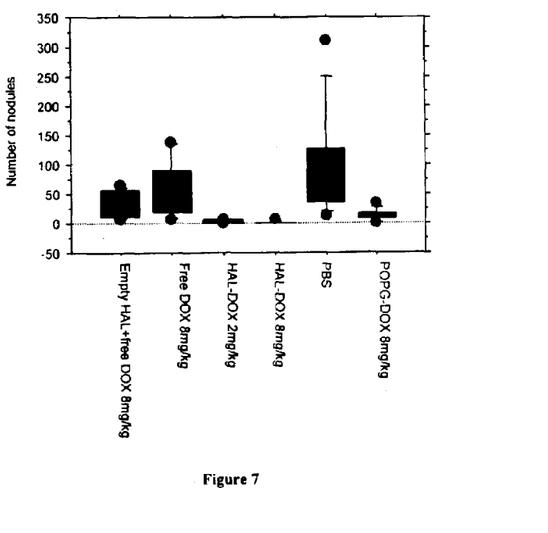
FIG. 7 is a bar graph of the number of tumor nodules following treatment with a delivery vehicle of the invention compared to free drug.
Figure 8:
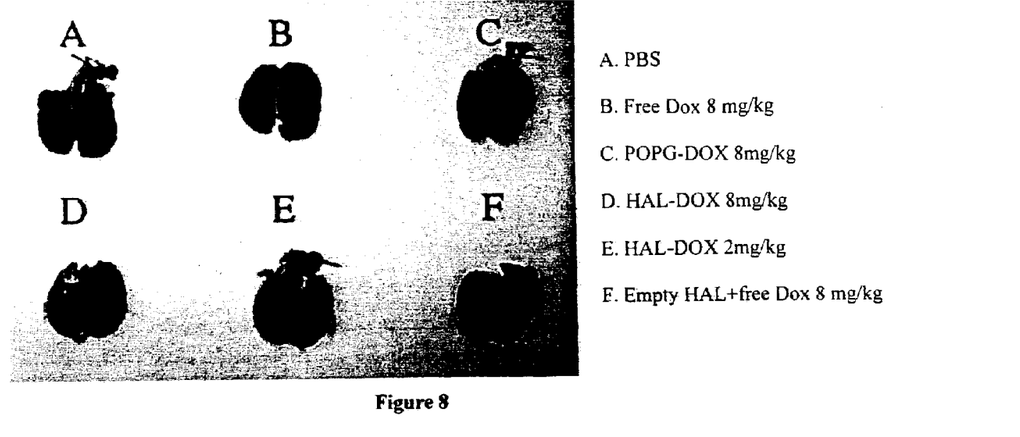
FIG. 8 is a picture of exemplary lung tumor nodules from the experiments shown in FIGS. 6 and 7.

FIGS. 6 and 7 are graphical representations of the data shown in Table 4. FIG. 6 is a scattered graph of the number of nodules in the lung by treatment. FIG. 7 is a bar graph of the number of nodules where the cross-lines in the bars in indicate the median of nodules in the lung. The upper limit of the each bar represents the 75% percentile while the lower limit of each bar represents the 25% percentile. All drug treatments reduced the number of tumor nodules. There is a trend for the liposome formulations to be better than non-encapsulated drug. The tumor nodules in the lung representative of each treatment group are shown in FIG. 8. The number of nodules was reduced significantly to an average of 1.1 and 2.9 nodules per lung with HAL-dox at drug concentrations of 8 and 2 mg/kg respectively. POPG vesicles containing doxorubicin at 8 mg/kg were also effective, with an average of 13.4 nodules per lung. It is evident that the HAL liposomes are effective in this model.

These experiments reveal that the targeted delivery vehicles of the invention distributed to the lung to a greater extent than the non-targeted liposomes. Furthermore, the drug carried by these delivery vehicles is more potent in cell culture than the free drug. These findings indicate that drugs delivered by the targeted delivery vehicles of the invention will be significantly more effective than other tested treatments.

Effect of Liposome Composition

As shown above, the presence of the targeting hyaluronan lipid, the type of lipid anchor that the hyaluronan was attached to and the lipid composition of the targeted liposomes influenced the anti-tumor effect. In this example, doxorubicin was encapsulated in liposomes of different compositions (described below in the liposome preparation) and injected into C57/BI6 mice at a dose of 3 mg/kg on day 6 after the mice had received the B16-F10 tumor as described above. First, it must be pointed out that the empty HAL plus free Dox was significantly better than the vehicle at reducing tumor nodules whereas the free drug was not significantly better than the vehicle. This suggests that the empty HAL liposomes by themselves had a slight tumor suppressive effect (Table 5). This is a novel and unexpected finding for a liposome associated ligand that does not contain drug.

The empty HAL plus free drug, POPG-Dox, HAL-POPE and HAL-DPPE formulations were statistically different than the vehicle control (Table 5). However only the two formulations containing the hyaluronan lipid were statistically different than the free drug and both exhibited a pronounced decrease in tumor nodules compared to vehicle or free drug (Table 5).

Moreover, both HAL containing formulations were statistically better in decreasing lung tumor nodules than the formulations that had a similar lipid composition but did not contain the hyaluronan lipid see HAL-POPE-Dox versus POPG-Dox and HAL-DPPE-Dox versus DSPG-Dox (Table 5). Thus the hyaluronan targeting lipid is the essential component for achieving the improved anti-tumor effect in this CD44 expressing tumor line.

TABLE 5

The effect of various formulations containing doxorubicin (Dox) on B16-F10 tumor nodules in the lung of C57/BI6 mice Doxorubicin concentration: 3 mg/kg (10 mice/group)

| Treatment group | # nodules Mean | # nodules Median | Statistic (p-value) Comparison to: PBS | Free drug |
|---|---|---|---|---|
| Vehicle (PBS) | 230.40 ± 79.74 | 249.5 | — | 0.1488 |
| Free drug | 171.60 ± 71.79 | 179 | 0.1488 | — |
| Empty HAL + Free drug | 148.10 ± 67.68 | 164 | 0.0162 | 0.3198 |
| PEG-DSPE-Dox | 168.20 ± 86.89 | 159 | 0.0670 | 0.6898 |
| DSPG-Dox | 165.90 ± 96.37 | 140 | 0.0577 | 0.6401 |
| POPG-Dox | 153.60 + 108.48 | 109.5 | 0.0245 | 0.4052 |
| HAL-POPE*-Dox | 3.70 ± 4.19 | 2 | <0.0001* | <0.0001* |
| HAL-DPPE*-Dox | 2.90 ± 3.25 | 2 | <0.0001* | <0.0001* |

Dose Response Relationship

Table 6 shows quantification of the dose response relationship of the free drug and the drug encapsulated in a hyaluronan targeted liposome in inhibiting tumor nodules in the B16-F10 lung tumor model. In this experiment groups of 10 animals were inoculated with the tumor cells on day zero and treated with the various formulations on day 6 as described above. To keep the lipid concentration constant as the dose of liposome encapsulated drug was reduced, HAL-Dox formulations were diluted with empty DSPG liposome (HSPC:Chol:DSPG 60:40:9 mole ration) to maintain the total lipid concentration at 1 micromole.

The first observation is that, the free drug group has a statistical significant effect only at the highest dose administered (10 mg/kg) (Table 6). This is in accord with the results presented in the previous two examples. The groups that received doxorubicin in the HAL-DPPE-Dox formulations showed a statistically significant decrease in tumor nodules in the lung even at a dose of 0.3 mg/kg (Table 6). Thus delivering the doxorubicin in the hyaluronan targeted liposome provides a reduction in lung tumor nodules as good as dose a thirty-three fold higher dose of the free doxorubicin. The results in these examples show conclusively that administering doxorubicin in liposomes that contain the hyaluronan lipid provides a statistically significant superior anti-tumor effect compared to other modes of administering the doxorubicin.

TABLE 6

Dose response of free Dox (0.3-10 mg/kg) and HAL-DPPE encapsulated Dox (0.1-3 mg/kg) on B16-F10 tumor nodules in the lung of C57/BI6 mice

| Treatment group | # nodules Mean | # nodules Median | Statistic (p-value) Comparison to: | |
|---|---|---|---|---|
| | | | PBS | Free drug 10 mg/kg |
| Vehicle (PBS) | 221 ± 108.9 | 276.5 | — | 0.0226 |
| Free drug 10 mg/kg | 157.9 ± 70.6 | 151 | 0.0226 | — |
| Free drug 3 mg/kg | 208.2 ± 82.1 | 191 | 0.6281 | 0.0696 |
| Free drug 1 mg/kg | 265.9 ± 34.5 | 277 | 0.1084 | 0.6898 |
| Free drug 0.3 mg/kg | 248.1 ± 56.9 | 250.5 | 0.3337 | 0.0015 |
| HAL-Dox 3 mg/kg | 2.5 ± 1.7 | 3 | <0.0001 | <0.0001 |
| HAL-Dox 1 mg/kg | 14.7 ± 7.6 | 14 | <0.0001 | <0.0001 |
| HAL-Dox 0.3 mg/kg | 87.1 ± 53.3 | 79.5 | <0.0001 | 0.0114 |
| HAL-Dox 0.1 mg/kg | 203.0 ± 52.7 | 206.5 | 0.5008 | 0.1031 |

Materials and Methods

Ligand Synthesis and Attachment

Bee venom hydrolysis of human umbilical cord hyaluronic acid (Sigma) is used to degrade high molecular weight hyaluronan into smaller fragments (4, 6 and 8 saccharides). Fragments are separated on 11×265 mm column of the formate form of Bio-Rad AG-3X4A ion-exchange resin (eluted with 270 ml portions of 0.015, 0.05, 0.15, 0.30, 0.50, 0.80 and 1.00 M formic acid). POPE-hyaluronan conjugates were prepared by a mixed solvent. This method employs reductive amination to the amino terminal portion of a phosphatidylethanolamine lipid—by reaction with sodium cyanoborohydride and saccharides fragments of hyaluronic acid. This generates a reactive carbonyl group capable of forming a single covalent bond. The product is preferably purified by silicic acid column chromatography.

Beyond the sizeable difficulty in identifying appropriate targeting ligands, discussed above, each new targeting ligand must be developed in parallel with its linkage chemistry to allow liposomal presentation while retaining the desired activity. A universal linkage system would greatly speed the development of new ligands.

Figure 9:
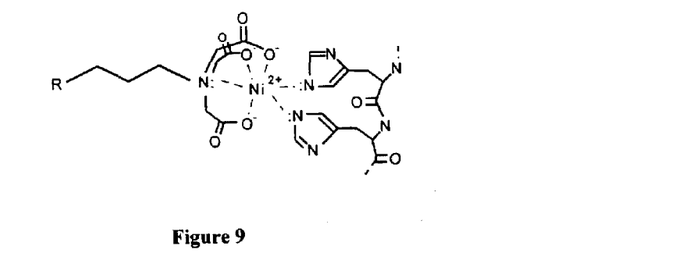
FIG. 9 shows the chelation of linking agents of the invention.

Use of chelated metals as peptide and protein linkages dates to the introductions of immobilized metal ion affinity chromatography (IMAC). In IMAC a metal ion, typically $Cu^{2+}$, $Zn^{2+}$ or $Ni^{2+}$ is chelated to an organic molecule presented on a chromatography resin. As shown in FIG. 9, nitrilotriacetic acid is a tetradentate chelator that can tightly bind $Ni^{2+}$ ($K_d$=0.1 pM), leaving two of six coordination sites for histidines. Although only two vicinal histidines are required for binding, a string of six histidines is often used to increase the probability of binding. Preferably, this invention comprises targeting ligands attached to six histidines. Reductive amination may also be used to attach the His-6 fragment to the lipid and to the Nitrotriacetic acid derivative of N-(1-carboxy-5-aminopentyl)iminodiacetic acid. The His 6 peptide and other peptide derivatives may be synthesized on an automated peptide synthesizer using FMOC solid phase chemistry. Further, the His-6 peptide and all other His-6 modified compounds may be purified using IMAC chromatography on a Qiagen NTA-Nickel column or by reverse phase HPLC.

An NTA-lipid conjugate has been successfully used to self-assemble protein layers at lipid monolayer interfaces. Accordingly, metal chelation technique should be an ideal method to couple ligands to liposomes. The advantages of this system include that the chemistry can be done on water soluble ligands in aqueous environments, the derivative purified on an NTA affinity column and the purified ligand attached to a preformed liposome. Indeed, a histidine-tagged peptide exhibits stable binding to an NTA-containing liposome.

For this exemplary embodiment, a histidine-6-tagged 20-mer peptide was synthesized. This peptide was functionalized with 4-nitrobenzo-2-oxa-1,3-diazole (NBD) to render it fluorescent. Liposomes were formed as described below with 3/4/58/35 NTA-lipid/POPG/POPC/Chol mole ratio. The excess NBD-histidine-peptide was added to a liposome preparation and agitated for 3 hours at room temperature. This solution was then separated on a size exclusion column to yield the liposome-peptide fraction. Peptide binding to the liposome is drastically reduced in the absence of NTA-lipid as well as under conditions of low pH (=4), where histidine residues are protonated. These controls provide compelling indirect evidence that the peptide-liposome binding is NTA-histidine mediated. Additionally, the peptide-liposome complex was relatively stable over a time period of 3 hours since approximately 80% of the peptide, as determined by fluoresce, was retained in the liposome fraction upon rechromatography of the complex. A hyaluronan-His 6 conjugate may be used following these examples to target delivery vehicles to cells expressing the CD44 receptor. For liposome embodiments, the His6 peptide can be attached to the hyaluronan and the NTA lipid embedded in the bilayer of the liposome or the hyaluronan can be attached to the NTA and the his6 peptide attached to a lipid and embedded in the bilayer.

The hyaluronan modified PEG lipid derivatives of the invention may be synthesized by methods known in the art. For example, sodium cyanoborohydride chemistry may be used to attach the oligosaccharide to an amino terminated PEG-lipid as follows. Amino-PEG-distearoylphosphatidylethanolamine was prepared form long circulation cationic liposomes containing amino-PEG-phosphatidylethanolamine. The 100 μmoles of amino-PEG-DSPE was deposited on the slides of a glass vessel from chloroform solution. The dried amino-PEG-DSPE was dispersed in 3 mL of 0.1M sodium carbonate pH 9.0 solution in water at 60° C. by placing the glass vessel in a bath sonicator (Lab Supply, Hicksville, N.Y.) for 5 minutes. Dry sodium cyanoborohydride (Sigma Chemicals, Inc. St. Louis, Mo.) was added to a final concentration of 0.3M to the amino-PEG-DSPE dispersion and incubated for 10 minutes at 60° C. At the end of the ten minutes, a solution containing 80 umoles of hyaluronan tetrasacchaaride in 3 mL of a buffer consisting of 1 M NaCl-0.1 M sodium carbonate pH 9.0 was added to the Mixture of amino-PEG-DSPE/sodium cyanoborohydride. The mixture was placed at 60° C. in the dark for 18 hours. At the end of this period the mixture was placed in a dialysis bag (6,000 to 8,000 molecular weight cut-off) and dialyzed against 600 mL of buffer consisting of 1.0 M NaCl-Hepes-pH 7.0 and dialyzed overnight at 4° C. After 18 hours the buffer outside the bag was replaced with 600 mL of 10 mM Hepes, pH 7.0 and the dialysis was continued for 24 hours at 4° C. The next day the buffer outside of the dialysis bag was replaced with 600 mL of deionized water and the dialysis was continued. The water dispersed material in the dialysis was removed, frozen and the water was removed in a lyophilyzer. The white dried powder was dissolved in 10 mL of chloroform/methanol: 7/3 and the material was fractionated on a silicic acid column developed with a chloroform and then a mixture of Chloroform/methanol: 7/3 volume to volume to elute the hyaluronan-amino-PEG-DSPE.

A convenient way to incorporate the hyaluronan-amino-PEG-DSPE derivative to the delivery vehicle is to make a water dispersion of the hyaluronan-amino-PEG-DSPE at 60° C. at a concentration of 10 mM and add it to a concentrated suspension of the preformed delivery vehicle, that is the liposome, micelle, emulsion or envelope virus so that the hyaluronan-amino-PEG-DSPE is added at a weight percent of between 0.02 to 20 weight percent and allow the system to stand for 60 minutes. Next, the temperature can be lowered to transfer the hyaluronan derivative from the aqueous dispersion into the delivery vehicle.

In the case of a virus, the hyaluronan can also be covalently incorporated by preparing a suspension of the virus at 1 mg viral protein per 2 mL in 0.1 M sodium carbonate pH 8.0 containing: 1 mg of hyaluronan oligomers. Then 1 mL of a solution of 0.3 M sodium cyanoborohydride in 1 M NaCl-0.1 M sodium carbonate pH 8.0 is added. The mixture is incubated for 8 hours at 37° C. At the end of the eight hour period the mixture is then placed in a dialysis bag of 50,000 molecular weight cut-off and dialyzed against 1000 mL of 0.15 M NaCl-10 mM hepes, pH 7.4 for 24 hours at 4° C. The hyaluronan modified virus can then be used to target to CD44 expressing cells.

Liposome Preparation

Liposomes may be prepared either as sonicated vesicles (small unilamelar vesicles—SUVs) or by the method of reverse-phase evaporation and extrusion through 0.1 μm polycarbonate membranes to increase the percentage encapsulation of the therapeutic agents. SUV—Liposomes will be prepared by drying 5 μmoles of lipid including POPE-hyaluronan from solvent (butanol saturated with distilled water) under vacuum rotoevaporation at room temperature, rehydrating the film with 1 ml of 10 mM HEPES, 5% glucose (pH 7.4), followed by vortex for 1 minute, sonication for 15 minutes under argon and extrusion through 0.1 μm polycarbonate membrane. The hydrodynamic diameter of the complex and liposomes may be determined by zeta-sizer (Malvern Instruments, Southborough, Mass.).

A specific, non-limiting example of doxorubicin loaded lipsome preparation involves thin lipid film hydration followed by sonication and extrusion. Briefly, the lipid components were weighed and dissolved in chloroform at the desired molar ratio(POPC:Chol:HA$_4$-POPE:aT 60:40:3:0.1; POPC:Chol:POPG:aT 60:40:9:0.1; HSPC:Chol:PEG-DSPE: aT 56.2:38.3:5.3:0.1; HSPC:Chol:DPPG:aT 56.2:38.3:5.3:0.1; HSPC:Chol:HA$_4$-DPPE:aT 56.2:38.3:5.3: 0.1). A thin lipid film was formed by removing the solvent on a rotary evaporator under vacuum in a 10 ml glass screw cap test tube. Each liposome batch consisted of 10 μmol phospholipid and was rehydrated in 250 mM ammonium sulfate. Hydration was done at room temperature for liposomes composed of POPC lipids and at 60° C. for liposomes composed of HSPC lipids. Hydration for both types of liposomes consisted of vigorous vortexing, 30 min of shaking on an incubator shaker (New Brunswick Scientific Co., Inc., Edison, N.J.) at a rate of 250 rpm and sonication for 15 min. Liposomes were repeatedly extruded (11 times) at room temperature for the POPC liposomes and at 60° C. for the HSPC liposomes through polycarbonate membranes of gradually decreasing pore size (0.2 and 0.1 μm). Extruded liposomes were dialyzed extensively against a 100-fold volume of a 5% glucose solution (four changes over a 24 h period). Doxorubicin (DOX) was actively transported into the liposome aqueous phase through the creation of ammonium sulfate gradient (22, 23). A 10 mg vial of DOX was dissolved in 5 ml of 5% glucose and then incubated for 2 h with the liposomes at 37° C. for the POPC liposomes and at 60° C. for the HSPC liposomes. Non-entrapped DOX was removed by passing the preparation through a column containing Dowex 50WX4. Phospholipid concentration was determined by a phosphorous assay. DOX concentrations were determined by measurement of absorbance at 480 nm (using a molar coefficient=12,500) after solubilization of the liposomes in 90% isopropyl alcohol containing 0.075 M HCl. DOX encapsulation efficiency was usually greater than 90%, with drug:phospholipid ratio of approximately 100 μg/μmol. For both POPC and HSPC liposomes, mean vesicle diameter as measured by dynamic light scattering using the multimodal program was 120-150 nm (SD<35% of the mean) with a monodisperse particle size distribution. In addition to incorporating a hyaluronan lipid derivative during the formation of the liposomes, the hyaluronan ligand may be attached to the liposome after formation.

ABREVIATIONS

The following abbreviations have been used:
aT, α-tocopherol.
Chol, Cholesterol.
DOX, Doxorubicin.
DPPE, Dipalmitoyl phosphatidylethanolamine.
DPPG, Dipalmitoyl phosphatidylglycerol.
FACS, Fluorescence-activated cell sorting.
FITC, fluorescein isothicyanate.
Hyaluronan, hyaluronic acid, HA.
HA-PE, Phosphatidylethanolamine lipid derivatives from β1,3 N-acetyl glucosaminyl-β1,4 glucuronide oligosaccharides.
HA4-PE, Hyaluronan tetrasaccharide conjugate with POPE.
HAL, Hyaluronan-targeted liposomes.
HAL-DOX, DOX-loaded HAL.
HSPC, hydrogenated soy phosphatidylcholine.
PEG-DSPE, polyethylene glycol conjugated to distearoyl phosphatidylethanolamine.
POPC, palmitoyl oleoyl phosphatidylcholine
POPG, palmitoyl oleoyl phosphatidylglycerol
POPE, palmitoyl oleoyl phosphatidylethanolamine
POPG-DOX, DOX-loaded non-target POPG liposomes.
SRB, sulforhodamine B.
TCA, trichloroacetic acid.

Described herein is a preferred embodiment, however, one skilled in the art that pertains to the present invention will understand that there are equivalent alternative embodiments.

What is claimed is:

1. A drug delivery system comprising an encapsulating delivery vehicle and a plurality of hyaluronan ligands, wherein each hyaluronan ligand has a molecular weight of less than 10,000 Daltons and each hyaluronan ligand is attached to the delivery vehicle by way of a single link, further comprising a therapeutic or diagnostic agent associated with the delivery vehicle.

2. The drug delivery system of claim 1, wherein the agent is an anticancer agent selected from the group consisting of doxorubicin, topotecan, gemcitabine, protein kinase C inhibitors, daunomycin, cisplatin, vinorelbine, cytosine arabinoside, vinblastine, vincristine, methotrexate, paclitaxel, fluoroorotic acid, N-(phosphonyl)L-aspartic acid, tomudex, irinotecan, camptothecin, octadecylphosphocholine, ether lipids, teniposide, docetaxel, mitomycin, indoloquinones, ormaplatin, staurosporine, bryostatin, mitoxantrone, oligonucleotides, polynucleotides, and DNA.

3. A method for delivering a therapeutic agent to a cell expressing the CD44 receptor comprising the step of contacting the cell with a composition comprising an encapsulating delivery vehicle and a plurality of hyaluronan ligands, wherein each hyaluronan ligand has a molecular weight of less than 10,000 Daltons and is attached to the delivery vehicle by way of a single link; further comprising an agent associated with the delivery vehicle, wherein said agent is selected from the group consisting of doxorubicin, topotecan, gemcitabine, protein kinase C inhibitors, daunomycin, cisplatin, vinorelbine, cytosine arabinoside, vinblastine, vincristine, methotrexate, paclitaxel, fluoroorotic acid, N-(phosphonyl)L-aspartic acid, tomudex, irinotecan, camptothecin, octadecylphosphocholine, ether lipids, teniposide, docetaxel, mitomycin, indoloquinones, ormaplatin, staurosporine, bryostatin, and mitoxantrone.

4. A method for delivering a therapeutic agent to a patient having cells that express the CD44 receptor, comprising the step of administering a composition comprising an encapsulating delivery vehicle and a plurality of hyaluronan ligands, wherein each hyaluronan ligand has a molecular weight of less than 10,000 Daltons and is attached to the delivery vehicle by way of a single link; further comprising an agent associated with the delivery vehicle, wherein said agent is selected from the group consisting of doxorubicin, topotecan, gemcitabine, protein kinase C inhibitors, daunomycin, cisplatin, vinorelbine, cytosine arabinoside, vinblastine, vincristine, methotrexate, paclitaxel, fluoroorotic acid, N-(phosphonyl)L-aspartic acid, tomudex, irinotecan, camptothecin, octadecylphosphocholine, ether lipids, teniposide, docetaxel, mitomycin, indoloquinones, ormaplatin, staurosporine, bryostatin, and mitoxantrone.

5. The method of claim 4, wherein the patient has lung cancer and the step of administering a composition comprises administering doxorubicin encapsulated by a liposome having hyaluronan lipid derivatives.

6. The method of claim 4, wherein the patient has cancer characterized by a solid tumor.

7. The method of claim 4, wherein the administering step is performed parenterally.

8. The method of claim 4, wherein the administering step is performed into airways of a lung of the patient.

9. The method of claim 4, wherein the administering step is performed topically.

* * * * *